United States Patent
Hagen et al.

(10) Patent No.: US 7,205,439 B2
(45) Date of Patent: Apr. 17, 2007

(54) PROCESS FOR THE PREPARATION OF DI- AND POLYAMINES OF THE DIPHENYLMETHANE SERIES

(75) Inventors: Torsten Hagen, Essen (DE); Stefan Grabowski, Dormagen (DE); Richard Adamson, Leichlingen (DE); Daniel Koch, Duisburg (DE); Stefan Wershofen, Mönchengladbach (DE)

(73) Assignee: Bayer Materialscience AG, Leverkusen (DE)

( * ) Notice: Subject to any disclaimer, the term of this patent is extended or adjusted under 35 U.S.C. 154(b) by 0 days.

(21) Appl. No.: 11/392,367

(22) Filed: Mar. 28, 2006

(65) Prior Publication Data

US 2006/0224018 A1  Oct. 5, 2006

(30) Foreign Application Priority Data

Mar. 30, 2005 (DE) .......................... 102005014244

(51) Int. Cl.
*C07C 209/78* (2006.01)
*C07C 263/10* (2006.01)

(52) U.S. Cl. .................. 564/333; 560/347; 564/315

(58) Field of Classification Search ........... 564/315, 564/333; 560/347
See application file for complete search history.

(56) References Cited

U.S. PATENT DOCUMENTS

| | | | |
|---|---|---|---|
| 3,517,062 A | 6/1970 | Powers | 260/570 |
| 5,310,769 A * | 5/1994 | Konig et al. | 521/163 |
| 6,433,219 B1 | 8/2002 | Ströfer et al. | 560/347 |
| 6,831,192 B2 | 12/2004 | Ströfer et al. | 560/347 |
| 2002/0132953 A1 | 9/2002 | Strofer et al. | 528/44 |
| 2004/0171869 A1 | 9/2004 | Reif et al. | 560/347 |
| 2005/0014975 A1 | 1/2005 | Strofer et al. | 564/330 |

OTHER PUBLICATIONS

Chem. Soc. Rev., 3(2), (month unavailable) 1974, p. 209-230, H.J. Twitchett, "Chemistry of the Production of Organic Isocyanates".
Kirk-Othmer Encycl. Chem. Technol., 3$^{rd}$ ed., 2, (month unavailable) 1978, pp. 338-348, M.V. Moore, "Methylenedianiline".
Wissenschaftliche Zeitschrift der TU Dresden, 38 (month unavailable) 1989, pp. 121-126, "Einfaches kinetisches Modell der Anilin-Formaldehyd-Kondensation".

* cited by examiner

*Primary Examiner*—Peter O'Sullivan
(74) *Attorney, Agent, or Firm*—Joseph C. Gil; Lyndanne M. Whalen

(57) ABSTRACT

Di- and polyamines of the diphenylmethane series are prepared by a) mixing a first portion of aniline with an acid catalyst, b) mixing a second portion of aniline with formaldehyde, and c) mixing and reacting the mixtures prepared in each of steps a) and b). The diamines produced by this process may then be phosgenated to produce the corresponding di-/polyisocyanate.

8 Claims, No Drawings

PROCESS FOR THE PREPARATION OF DI- AND POLYAMINES OF THE DIPHENYLMETHANE SERIES

BACKGROUND OF THE INVENTION

The invention relates to a process for the preparation of di- and polyamines of the diphenylmethane series (MDA) by reaction of aniline with formaldehyde in the presence of acid catalyst, in which a first portion of the aniline is mixed with acid catalyst and a second portion of the aniline is mixed with formaldehyde, and these mixtures are then mixed with one another and reacted.

The preparation of MDA is generally known and is conventionally carried out by reaction of aniline with formaldehyde in the presence of acid catalysts in a continuous, semi-continuous or discontinuous process. The process is described in numerous patents and publications (see e.g. H. J. Twitchett, Chem. Soc. Rev. 3(2), 209 (1974), M. V. Moore in: Kirk-Othmer Encycl. Chem. Technol., 3rd ed., New York, 2, 338–348 (1978)).

Polyamines of the diphenylmethane series (MDA) are understood as meaning amines and mixtures of amines of the following type:

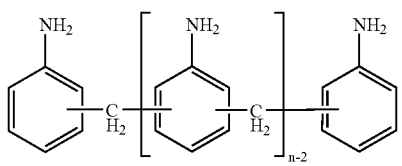

wherein n represents a natural number $\geq 2$.

In the reaction of aniline and formaldehyde, a mixture of isomers is conventionally formed, because the $CH_2$ group can substitute the aromatic ring of the aniline in the 2 position and/or 4 position and/or 6 position. A mixture of homologues is furthermore formed in this reaction, since n molecules of aniline can react with (n−1) molecules of formaldehyde to give a polyamine of chain length n. The composition of the isomer and homologue mixture varies according to the reaction conditions and the recipe used. In general, a high content of 4,4'-MDA (n=2) in the reaction product is desirable.

A number of methods are known for increasing the selectivity in favor of 4,4'-MDA. For example, an increase in the specific concentration of acid catalyst in the reaction mixture, an increase in the aniline excess and low reaction temperatures lead to an increase in the yield of 4,4'-MDA. Thus, e.g., DE-A-1 643 449 describes the preparation of MDA with a high content of 4,4'-MDA by reaction of aniline which has been reacted with acid beforehand with formaldehyde, the degree of protonation being at least 25%, preferably at least 50%, and even better 75–100%. DE-A-10 111 337 describes the preparation of MDA with a degree of protonation of <20%, MDA having an increased content of 2,4' isomer nevertheless being obtained. EP-A-10 53 222 reports that a high temperature leads to MDA with an increased content of 2,4' and 2,2' isomers.

All of the known measures for increasing the selectivity in favor of 4,4'-MDA have the disadvantage, however, that the profitability of the process becomes lower. A higher specific amount of acid catalyst employed increases the material costs, since the catalyst is removed by neutralization during the working up and is therefore consumed. The excess amount of aniline lowers the space/time yield and increases the energy consumption during the redistillation. Lower reaction temperatures require longer reaction times in order to bring the conversion to completion.

A considerable difficulty in the industrial implementation of this process is that the chemical reactions are highly exothermic and the selectivity-determining reaction steps are very fast (H.-J. Ladwig, W. Pippel, C. Ringel, H. Oelmann, "Einfaches kinetisches Modell der Anilin-Formaldehyd-Kondensation", Wissenschaftliche Zeitschrift der TU Dresden, 38, 1989, p. 121–126). This means that these reactions already proceed at least in part during the thorough mixing of the reactants and local temperature and concentration gradients, which reduce the selectivity, can thereby occur. For example, elevated temperatures during the mixing of formaldehyde with a reaction mixture which contains aniline and acid catalyst lead to an increase in the content of higher oligomers or ortho isomers. However, the methods known to date for suppressing selectivity losses on the basis of temperature peaks during mixing are not sufficiently effective.

SUMMARY OF THE INVENTION

The object of the present invention is therefore to provide a simple and economical process for the preparation of MDA in which the formation of undesirable isomers, homologues or by-products is prevented or suppressed.

This and other objects which will be apparent to those skilled in the art are accomplished by combining a first portion of the aniline to be reacted with acid catalyst and a second portion of the aniline to be reacted with formaldehyde. The first and second portions of aniline are then combined and reacted.

DETAILED DESCRIPTION OF THE INVENTION

The invention is directed to a process for the preparation of di- and polyamines of the diphenylmethane series in which a) a first portion of aniline is mixed with an acid catalyst, and
b) a second portion of aniline is mixed with formaldehyde, and
c) the mixtures prepared in steps a) and b) are then mixed with one another and reacted.

The advantage of the process according to the invention is that by dividing the mixing into the three steps a), b) and c) the total resulting heat of mixing and reaction which arises is likewise distributed over these three steps. The heat of mixing and reaction which arises in each of the individual steps a), b) and c) is thus relatively low compared with a process in which these three steps are not carried out separately in the manner required in the present invention.

The process of the present invention is of particular advantage when high throughputs of mixtures produced in step c) of preferably greater than 5 $m^3/h$, most preferably greater than 10 $m^3/h$, or if a large apparatus (i.e., apparatus with a volume of greater than 3 $m^3$, most preferably of greater than 5 $m^3$) is used for carrying out the mixing and/or the reaction in step c), because in such large apparatus the ratio of surface area to volume is in general reduced and the cooling capacity is therefore limited and adequate external cooling can be realized only with expensive technical means.

In this context, cooling can be carried out by removing the heat of reaction via the outer wall of the reactor through a cooling jacket. The cooling medium employed is preferably cooling water having a temperature of 2–45° C., most preferably 20-35° C. It is also possible to use reactors having a pumped circulation and a heat exchanger integrated therein. It is furthermore possible to use reactors with a vacuum system and a heat exchanger integrated therein (evaporative cooling). It is possible to use one of these cooling possibilities or combinations of these cooling possibilities. In this context, the total cooling capacity available is composed of the cooling capacities through the wall surfaces of the reactor, of the heat exchanger installed in the circulation and of the heat exchanger installed in the vapor system.

In particular, however, it is of advantage that no selectivity-determining reactions proceed in step a) and b). The increase in temperature which may occur in each of steps a) and b) as a result of the heat of reaction released does not lead to a reduction in the selectivity. The heat of reaction from each of steps a) and b) can be removed, e.g., by cooling, and the mixtures formed from a) and b) can be fed at a low temperature to the mixing step c).

Suitable temperatures for the mixing in step a) are in the range of from 0 to 100° C., preferably in the range of from 20 to 95° C. Suitable temperatures for the mixing in step b) are in the range of from 20 to 100° C., preferably from 40 to 100° C., most preferably from 60 to 95° C. The selectivity-determining reactions proceed only during or after the mixing in step c). Suitable temperatures for the mixing in step c) are in the range of from 20° C. to 250° C. Preferably, during the mixing in step c), the temperature is kept in the range of from 20 to 100° C., preferably from 20 to 80° C., most preferably from 20 to 60° C. This can be achieved by external cooling and/or by adjusting the temperature of the mixtures employed, which have been obtained beforehand in steps a) and b). Preferably, the mixture obtained in step a) is used at a temperature of from 15 to 100° C., most preferably from 20 to 60° C. Preferably, the mixture obtained in step b) is used at a temperature of from 40 to 130° C., most preferably from 50 to 100° C. Thereafter, the temperature is increased, optionally after a pre-reaction time of from 0 to 100 min at a temperature of from 20 to 100° C., preferably 30 to 95° C., continuously or in stages up to a final temperature of from 90 to 250° C., preferably 100 to 160° C.

The process of the present invention is particularly advantageously carried out on a large scale as described above, since the devices required for removal of the heat may involve less outlay. In this context, the cooling capacity required, for the sum of steps a), b) and c), is preferably>500 kW, most preferably>1,000 kW. Since steps a) and b), which are not selectivity-determining, are preferably carried out at 20 to 95° C. and, 60 to 95° C., respectively, but the selectivity-determining step c) is carried out at a lower temperature of preferably 20 to 60° C., at a given cooling water temperature of from 20 to 35° C. As a result, for a particular cooling capacity a heat exchanger having a smaller heat exchanger area is sufficient. In the process according to the invention, the sum of the heat exchanger areas required for steps a), b) and c) is lower than in a process in which these three steps are not carried out separately and the total heat must be removed at a lower temperature and at a smaller temperature difference from the cooling medium.

The total duration of the reaction is conventionally between 30 and 750 min, preferably from 50 to 300 min, most preferably from 90 to 180 min. The essential advantage of the process of the present invention is that the residual heat of reaction released in step c) is only part of the total heat of reaction, since the other part of the heat of reaction has already been released in steps a) and b), which are not selectivity-determining. Side reactions as a result of temperature peaks during mixing are therefore effectively suppressed. This effect is also particularly advantageous when carrying out the process on a large scale, as described above, since the apparatuses employed for the mixing may involve less outlay.

The process can in general be carried out continuously, semi-continuously or discontinuously. Suitable apparatuses for carrying out the reaction in step c) are, for example, stirred reactors, tube reactors and also tube reactors with baffles, such as perforated trays, which influence the dwell time characteristics in the reactor. A combination of several reactor types is also suitable. The absolute reaction pressure is conventionally in the range of from 0.01 bar to 10 bar, preferably in the range of from 0.03 bar to 5 bar.

Suitable acid catalysts are strong organic or inorganic acids such as hydrochloric acid, sulfuric acid, phosphoric acid, methanesulfonic acid or solid acids, such as zeolites. Hydrochloric acid is preferably employed.

The concentrations and concentration ratios of the starting compounds and of the auxiliary substances can in principle be freely chosen. Conventionally, aniline is employed as a technical-grade product having a content of from 85 to >99 wt. %, formaldehyde as an aqueous solution having a content of from 20 to 50 wt. % and hydrochloric acid as an aqueous solution having a content of from 20 to 37 wt. %. However, it is also possible to employ aqueous formaldehyde solution of another concentration or other compounds which supply methylene groups, such as polyoxymethylene glycol, para-formaldehyde or trioxane. Aniline is conventionally employed in an excess with respect to formaldehyde, the molar excess of aniline being in the range of from 1.5 to 10, preferably 1.8 to 5. The molar amount of hydrochloric acid is conventionally in the range of from 1 to 50%, based on the molar amount of aniline employed, preferably 5 to 30%. The division of the amount of aniline between steps a) and b) is in principle as desired. From practical considerations, however, a concentration precipitation of anilinium hydrochloride at the desired reaction temperature is to be avoided where possible. The increasing viscosity of mixture b) as the aniline:formaldehyde ratio decreases also restricts the operating range in step b). For the preparation of certain product types it may therefore be advantageous to add an additional amount of formaldehyde to the reaction mixture after the mixing in step c), in addition to the amount of formaldehyde mixed with aniline in step b).

Aniline is therefore preferably employed in the ratio of from 1:1 to 1:9 distributed over steps a) and b).

The mixture prepared in step b) is as a rule two-phase. The aqueous phase can be separated off in an additional separating step, or left in the mixture. Preferably, the water is separated off, e.g. by phase separation.

The reaction can be carried out in undissolved form or in a solvent. Suitable solvents are, for example, water, alcohols or substituted or unsubstituted aromatic hydrocarbons. The reaction is preferably carried out without addition of a solvent.

It is also possible to add aniline, formalin or acid catalyst after the mixing in step c).

For working up the acid reaction mixture obtained in step c), the reaction mixture is conventionally neutralized with a base according to the prior art. According to the prior art, the neutralization is conventionally carried out at temperatures of, for example, from 90 to 100° C. without addition of further substances (H. J. Twitchett, Chem. Soc. Rev. 3(2), 223 (1974)). However, it can also be carried out at another temperature level, in order, e.g., to accelerate the breakdown of troublesome by-products. Suitable bases are, for example, the hydroxides of the alkali metal and alkaline earth metal elements. Aqueous NaOH is preferably used.

The base employed for the neutralization is preferably employed in amounts greater than 100%, most preferably 105 to 120% of the stoichiometrically required amount for neutralization of the acid catalyst employed.

After the neutralization, the organic phase is conventionally separated from the aqueous phase in a separating vessel. The product-containing organic phase which remains after the aqueous phase has been separated off is preferably subjected to further working up steps (e.g. washing) and then freed from excess aniline and other substances present in the mixture (e.g. further solvents) by suitable processes, such as distillation, extraction or crystallization.

The present invention also relates to a process for the preparation of di- and polyisocyanates of the diphenylmethane series, in which a) a first portion of aniline is mixed with an acid catalyst, and
b) a second portion of aniline is mixed with formaldehyde, and
c) the mixtures prepared in step a) and b) are then mixed with one another and reacted to give di- and polyamines of the diphenylmethane series, and subsequently
d) the di- and polyamines of the diphenylmethane series produced in step c) are reacted with phosgene to give di- and polyisocyanates of the diphenylmethane series.

In this process, the MDA prepared in accordance with the present invention is reacted with phosgene in an inert organic solvent by any of the known methods to give the corresponding isocyanates. The molar ratio of crude MDA to phosgene is generally from 1 to 10 mol, preferably 1.3 to 4 mol of phosgene per mol of $NH_2$ groups present in the reaction mixture. Suitable inert solvents are chlorinated, aromatic hydrocarbons, such as e.g. monochlorobenzene, dichlorobenzenes, trichlorobenzenes, the corresponding toluenes and xylenes as well as chloroethylbenzene. Monochlorobenzene, dichlorobenzene or mixtures of these chlorobenzenes are particularly useful as inert organic solvents. The amount of solvent is expediently chosen so that the reaction mixture has an isocyanate content of from 2 to 40 wt. %, preferably between 5 and 20 wt. %, based on the total weight of the reaction mixture. When the phosgenation has ended, the excess phosgene, the inert organic solvent or mixtures thereof are separated off from the reaction mixture by distillation.

From the crude MDI obtained, the products of the polymeric MDI series which include di- and polyisocyanates of the diphenylmethane series which are dinuclear and more than dinuclear, and of the monomeric MDI series, including dinuclear diisocyanate of the diphenylmethane series, can be prepared, in particular high-viscosity polymeric MDI types of 80 to 3,000 mPas at 25° C., technically pure 4,4'-MDI and/or technically pure 2,4'-MDI as well as mixed forms thereof. These products can be separated off from the crude MDI by any of the processes known to those skilled in the art, for example, by distillation. These products are suitable for use as raw materials for polyurethane preparation in the form of polymers and prepolymers by reaction with polyols.

Having thus described the invention, the following Examples are given as being illustrative thereof.

EXAMPLES

General Description of the Experiments:

The following starting substances were mixed with one another in a laboratory glass apparatus equipped with a stirrer and a cooling bath with ice-water.

| | Content | Amount weighed | Amount of substance |
|---|---|---|---|
| Aniline | >99.9 wt. % | 465.7 g | 5.00 mol |
| Formaldehyde solution | 30.12 wt. % (HCHO) | 178.0 g | 1.79 mol |
| Hydrochloric acid | 32.74 wt. % (HCl) | 111.5 g | 1.00 mol |

After mixing was completed in the individual examples, the temperature of the mixture was 50° C. The cooling bath was then replaced by an electric heating jacket and the mixture was heated up to 75° C. in the course of 10 min. The mixture was stirred at 75° C. for 30 min and then heated to the boiling point under reflux in the course of 30 min. The internal temperature was 103 to 105° C. After 10 hours under reflux, 148.6 g of 32.3% strength sodium hydroxide solution and 133 ml dist. water were added. A two-phase mixture was formed during this operation, and was stirred intensively for 15 min. Thereafter, the phases were separated and the organic phase was extracted twice more with 400 ml distilled water each time. Excess aniline and residues of water were separated off from the organic phase by distillation in vacuo (0.1 mbar). The product MDA was obtained as the bottom product of the distillation. The composition thereof was determined by reverse phase HPLC.

Description of the Mixing:

Example 1 (Comparison Example)

Semi-Batch Procedure: Feeding of Formaldehyde Solution into the Aniline Hydrochloride in the Receiver The aniline (25° C.) was initially introduced into the apparatus for the experiment. The hydrochloric acid (25° C.) was added to this, while stirring. A clear solution was formed during this operation. The temperature rose to 53° C. during this operation. The mixture was temperature-controlled at 50° C. The formaldehyde solution (25° C.) was then added dropwise in the course of 10 min, while stirring, and the mixture was then subsequently stirred for a further 5 min. During the metering, the mixture was cooled with an ice-water bath. The internal temperature rose temporarily to 51.0° C.

Example 2 (Comparison Example)

Simultaneous Feeding of Formaldehyde+HCl into the Aniline Initially Introduced

The aniline was initially introduced into the apparatus for the experiment and was temperature-controlled at 50° C. The hydrochloric acid (25° C.) and the formaldehyde solution (25° C.) were simultaneously added dropwise to this at a constant rate in the course of 10 min, while stirring, and the mixture was then subsequently stirred for a further 5 min. During the metering, the mixture was cooled with an ice-water bath. The internal temperature rose temporarily to 61.5° C.

Example 3 (Comparison Example)

Semi-Batch Procedure: HCl Feed into the Aniline/Formaldehyde Mixture in the Receiver Variant I:

The aniline and the formaldehyde solution were mixed with one another, while stirring. Two phases were formed during this operation, and were separated from one another. The organic phase was initially introduced into the apparatus for the experiment and was temperature-controlled at 50° C. The hydrochloric acid (25° C.) was added dropwise to this in the course of 15 min, while stirring, and the mixture was then subsequently stirred for a further 10 min. During the metering, the mixture was cooled with an ice-water bath. The internal temperature rose temporarily to 66.8° C.

Variant II:

Only half of the organic phase from the mixing of formaldehyde solution with aniline was initially introduced into the reaction vessel. The other half was added dropwise simultaneously with the hydrochloric acid.

Variant III:

The procedure was as in Variant II. Instead of being cooled with an ice-water bath, however, the reaction mixture was cooled by evaporative cooling under a pressure of 60–80 mbar. At no point in time did the internal temperature rise above 50.0° C.

Example 4 (Example According to the Invention)

Aminal Semi-Batch: Feeding of Aminal into the Anilinium Hydrochloride Initially Introduced Variant I:

¾ of the aniline and the formaldehyde solution were mixed with one another, while stirring. Two phases formed during this operation, and were separated from one another. The organic phase (=aminal) was transferred into a temperature-controlled pump receiver and was temperature-controlled at 80° C.

¼ of the aniline (25° C.) was initially introduced into the apparatus for the experiment. The hydrochloric acid (25° C.) was added to this, while stirring. A clear solution (=anilinium hydrochloride) formed during this operation. The temperature rose temporarily to approx. 70° C. The mixture was temperature-controlled at 50° C. The aminal was then pumped in, while stirring, in the course of 10 min and the mixture was then subsequently stirred for a further 5 min. During the metering, the mixture was cooled with an ice-water bath. The internal temperature rose temporarily to 50.8° C.

Variant II:

The metering time was 30 min

Variant III:

The metering time was 60 min

Example 5 (Example According to the Invention)

Aminal Semi-Batch: Simultaneous Feed of Aminal+Anilinium HCl

The procedure was as in Example 4, but only half of the anilinium hydrochloride solution prepared (i.e. in total only half of ¼ of the aniline) is left in the receiver.

The other half is transferred into a dropping funnel and metered into the reaction mixture simultaneously with the aminal.

The compositions of the products obtained in these Examples are reported in Table 1.

TABLE 1

| Example | 4 | | | | | | 3* | | |
|---|---|---|---|---|---|---|---|---|---|
| Variant | I | II | III | 5 | 1* | 2* | I | II | III |
| Residual aniline [wt. %] | 0.08 | 0.08 | 0.20 | 0.20 | 0.15 | 0.08 | 0.16 | 0.27 | 0.00 |
| 4,4'-MDA [wt. %] | 64.9 | 64.8 | 65.4 | 64.7 | 64.1 | 62.9 | 58.4 | 61.2 | 63.9 |
| N-Formyl-MDA [wt. %] | 0.26 | 0.22 | 0.21 | 0.30 | 0.31 | 0.32 | 0.70 | 0.49 | 0.35 |
| 2,4'-MDA [wt. %] | 6.6 | 6.5 | 6.5 | 6.7 | 7.5 | 8.1 | 9.1 | 7.6 | 7.0 |
| 2,2'-MDA [wt. %] | 0.28 | 0.28 | 0.29 | 0.29 | 0.36 | 0.42 | 0.64 | 0.42 | 0.34 |
| N-Methyl-MDA [wt. %] | 0.31 | 0.25 | 0.21 | 0.27 | 0.26 | 0.31 | 0.77 | 0.49 | 0.34 |
| Σ higher MDA homologues (n > 2) [wt. %] | 25.5 | 25.6 | 25.9 | 26.0 | 25.7 | 26.5 | 27.0 | 27.1 | 27.0 |
| Σ unknown [wt. %] | 2.0 | 2.2 | 1.3 | 1.6 | 1.6 | 1.4 | 3.2 | 2.4 | 1.1 |
| 4,4'-MDA/2,4'-MDA [weight ratio] | 9.9 | 10.0 | 10.0 | 9.6 | 8.5 | 7.8 | 6.4 | 8.1 | 9.2 |
| 4,4'-MDA/2,2'-MDA [weight ratio] | 232 | 232 | 225 | 223 | 178 | 150 | 91 | 146 | 188 |

*Comparative Example

The results of the experiments show the advantages of the process according to the invention:

higher content of monomeric 4,4'-MDA in the end product
higher para-selectivity (measured as the weight ratio of 4,4'-MDA:2,4'-MDA and as the weight ratio of 4,4'-MDA: 2,2'-MDA; more para isomer is advantageous)

Excess concentrations and temperature peaks at the site of the reaction are effectively prevented by the invention, without particular expensive technical equipment being necessary.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a di- and/or polyamine of the diphenylmethane series comprising:
    a) mixing a first portion of aniline with an acid catalyst to form a first mixture,
    b) mixing a second portion of aniline with formaldehyde to form a second mixture,
    c) mixing the mixture of step a) with the mixture of b) to form a third mixture, and d) reacting the mixture of step c) to form a di- and/or polyamine of the diphenylmethane series.

2. The process of claim 1 in which the some or all of any aqueous phase is first separated off from the mixture prepared in step b) before mixing it with the mixture prepared in step a).

3. The process of claim 1 in which additional formaldehyde is added to the mixture formed in step c).

4. The process of claim 1 in which the mixing in step c) is carried out semi-continuously.

5. The process of claim 1 in which hydrochloric acid is the acid catalyst used in step a).

6. The process of claim 1 in which step c) and/or step d) is carried out in an apparatus having a volume greater than 3 m$^3$.

7. The process of claim 1 in which the total cooling capacity required for steps a), b), c) and d) is greater than 500 kW.

8. A process for the preparation of a di- and/or polyisocyanate of the diphenylmethane series comprising:
   a) mixing a first portion of aniline with an acid catalyst to form a first mixture,
   b) mixing a second portion of aniline with formaldehyde to form a second mixture,
   c) mixing the mixtures prepared in step a) and b) with one another to form a third mixture,
   d) reacting the mixture from c) to form a di- and/or polyamine of the diphenylmethane series, and
   e) phosgenating the di- and polyamines of the diphenylmethane series formed in step d) to form a di- and/or polyisocyanate of the diphenylmethane series.

* * * * *